(12) United States Patent
Venturini et al.

(10) Patent No.: US 12,733,962 B2
(45) Date of Patent: Sep. 15, 2026

(54) TELESCOPIC NAIL AND ASSOCIATED PERFORATING TOOL

(71) Applicant: ORTHOFIX S.R.L., Bussolengo (IT)

(72) Inventors: Daniele Venturini, Veronese (IT); Georges Fernand Jacques Finidori, Paris (FR); Zagorka Pejin, Paris (FR)

(73) Assignee: Orthofix S.R.L., Bussolengo (IT)

( * ) Notice: Subject to any disclaimer, the term of this patent is extended or adjusted under 35 U.S.C. 154(b) by 24 days.

(21) Appl. No.: 19/045,118

(22) Filed: Feb. 4, 2025

(65) Prior Publication Data

US 2025/0195114 A1 Jun. 19, 2025

Related U.S. Application Data

(63) Continuation of application No. 17/799,376, filed as application No. PCT/EP2020/055563 on Mar. 3, 2020, now Pat. No. 12,357,353.

(30) Foreign Application Priority Data

Mar. 6, 2019 (IT) ........................ 102019000003285

(51) Int. Cl.
*A61B 17/72* (2006.01)
*A61B 17/00* (2006.01)
(Continued)

(52) U.S. Cl.
CPC *A61B 17/7233* (2013.01); *A61B 2017/00991* (2013.01); *A61B 17/1662* (2013.01);
(Continued)

(58) Field of Classification Search
CPC .. A61F 17/72; A61F 17/7216; A61F 17/7241; A61F 17/725; A61F 17/7233;
(Continued)

(56) References Cited

U.S. PATENT DOCUMENTS 5,704,939 A * 1/1998 Justin ................ A61B 17/7216 606/62
6,336,929 B1 1/2002 Justin
(Continued)

FOREIGN PATENT DOCUMENTS

WO 2016175729 A1 11/2016

OTHER PUBLICATIONS

European Patent Office, International Searching Authority, International Search Report and Written Opinion of PCT/EP2020/055563, dated Jul. 10, 2020, 12 pages.

*Primary Examiner* — Marcela I. Shirsat
(74) *Attorney, Agent, or Firm* — Haynes and Boone, LLP

(57) ABSTRACT

A method for implanting a telescopic nail may include providing a telescopic nail comprising a hollow stem, a rod inserted telescopically into the hollow stem, a first fastening element configured to couple to an end of the hollow stem for fixing to a first long bone end, and a second fastening element configured to couple to an end of the rod for fixing to a second long bone end. The end of the hollow stem couples to a coupling end of a perforating tool. The method further includes the steps of inserting the perforating tool opposite to the coupling end inside the cavity, coupling the end of the hollow stem of the telescopic nail together with a counter-coupler of the coupling end of the perforating tool, and advancing the perforating tool inside the cavity until it comes out completely from the other long bone end.

19 Claims, 17 Drawing Sheets

(51) Int. Cl.

| | |
|---|---|
| ***A61B 17/16*** | (2006.01) |
| ***A61B 17/17*** | (2006.01) |
| ***A61B 17/56*** | (2006.01) |
| ***A61B 17/86*** | (2006.01) |
| ***A61B 17/88*** | (2006.01) |
| ***A61B 17/92*** | (2006.01) |
| ***A61F 2/28*** | (2006.01) |
| ***A61F 2/36*** | (2006.01) |
| ***A61F 2/46*** | (2006.01) |

(52) U.S. Cl.

CPC ....... *A61B 17/1668* (2013.01); *A61B 17/1717* (2013.01); *A61B 17/1725* (2013.01); *A61B 2017/564* (2013.01); *A61B 17/7216* (2013.01); *A61B 17/7225* (2013.01); *A61B 17/7241* (2013.01); *A61B 17/725* (2013.01); *A61B 17/8615* (2013.01); *A61B 17/862* (2013.01); *A61B 17/864* (2013.01); *A61B 17/8883* (2013.01); *A61B 17/8888* (2013.01); *A61B 17/921* (2013.01); *A61F 2002/2825* (2013.01); *A61F 2/3662* (2013.01); *A61F 2/4607* (2013.01)

(58) Field of Classification Search

CPC ................ A61F 17/164; A61F 17/7225; A61F 17/1662; A61F 17/1668; A61F 17/86; A61F 17/864; A61F 17/8615; A61F 17/862; A61F 17/8883; A61F 17/8888; A61F 17/1717; A61F 17/1725; A61F 17/92; A61F 17/921; A61F 2002/2825; A61F 2002/28; A61F 2002/2892; A61F 2/3662; A61F 2/4607; A61B 2017/00991; A61B 2017/564

USPC .................... 606/329, 60, 62, 63, 64, 67, 86

See application file for complete search history.

(56) References Cited

U.S. PATENT DOCUMENTS

| | | | | |
|---|---|---|---|---|
| 6,524,313 | B1 | 2/2003 | Fassier | |
| 2006/0015123 | A1 * | 1/2006 | Fencl | ................ A61B 17/1725 606/104 |
| 2011/0313473 | A1 | 12/2011 | Prandi | |
| 2013/0165980 | A1 | 6/2013 | Cook | |

* cited by examiner 1
2
10
20
30

1
2
4
5
10
11
12
20
30

5
2
4

31
3
31

30
10
12

30
11
10
2

51
50
30
10

703
700
701
702
705

700
704

TELESCOPIC NAIL AND ASSOCIATED PERFORATING TOOL

PRIORITY

This application is a continuation application of U.S. patent application Ser. No. 17/799,376, filed Aug. 12, 2022, which is a national phase application of PCT/EP2020/055563, filed Mar. 3, 2020, which claims priority to and the benefit of Italy Application 102019000003285, filed Mar. 6, 2019, all of which are incorporated herein in their entireties.

FIELD OF THE INVENTION

The present invention relates to a telescopic nail which can be inserted into the long bones of a patient and to a perforating tool for the implant of the nail. This nail is of the type comprising a hollow stem which can be fixed to the end of a long bone and a rod which can be fixed to the other end of the long bone and is slidably inserted into the hollow stem.

The invention relates, in particular, but not exclusively, to a telescopic nail intended for the treatment of fractures or deformations of long bones, as for example in the case of osteogenesis imperfecta or pseudo-arthrosis.

The invention has a useful application in the sector of paediatric orthopaedics, for example for the correction of bone deformations of long bones due to osteogenesis imperfecta or congenital pseudo-arthrosis. Therefore, the description which follows is provided with reference to the non-limiting use in the context of this sector.

PRIOR ART

Known techniques for correcting long bone deformations in patients at a growing age affected by osteogenesis imperfecta involve carrying out at least one osteotomy, alignment of the bone stumps and insertion of a nail into a cavity or channel formed beforehand along the bone.

The nails used in this type of operation are of the telescopic type, namely they have a hollow stem which can be fixed to the end of a long bone and a rod which can be fixed to the other end of the long bone and is slidably inserted into the hollow stem. The sliding of the two components during the growth of the bone allows the nail to adapt to the variation in length of the said bone, while maintaining the alignment.

Telescopic nails according to the prior art of the Bailey-Dubow, Sheffield and Interlocking type have at the free end of the rod and the hollow stem an element transverse to the axis of the nail designed to bear against the corresponding end of the bone, preventing the component from penetrating into the bone itself.

Although this type of nail has dimensions such as to minimize the interference with the growth cartilage, they do not ensure an adequate fixing action and rotational stability of the ends of the nail during the bone growth. The transverse element only prevents the nail from penetrating into the bone but does not constrain the other degrees of freedom.

The drawback associated with the stability has been dealt with in the prior art by providing a threading at the end of the nail which can be fixed to the bone by means of screwing, for instance as disclosed in the PCT patent application NO. WO 2016/175729 A1 or in the U.S. Pat. No. 6,524,313 B1.

In particular, this second type of telescopic nail, such as the Fassier-Duval nail, comprises a rod having a threaded tip designed to be screwed into an epiphysis of the long bone and a hollow stem having a threaded head which can be screwed into the opposite epiphysis.

Although the threaded ends of the Fassier-Duval nail ensure an adequate fixing stability, they penetrate into the growth cartilage with a volume such as to negatively affect the homogeneous growth of the bone.

From that stated above it is clear that there exists the need to develop a telescopic nail which is able to ensure an adequate stability of the implant and to minimize the interference with the growth cartilage.

The nails of this second type are usually implanted by means of two alternative surgical techniques.

The first technique, which is more invasive, involves the formation of an access point on the bone diaphysis, exposure of the bone, execution of the osteotomy operations, and drilling of the single bone stumps by means of a perforator in order to form the cavity inside which the nail will be housed.

The other technique involves instead the execution of the osteotomy operations percutaneously during the advancing movement, along the bone, of the perforator introduced into one of the ends of the said bone.

In both surgical techniques, once the cavity has been formed, the perforator is removed.

Then the rod is inserted into the cavity at one end of the bone until the threaded tip is screwed inside the epiphysis of the opposite end. The hollow stem is then inserted into the cavity so as to slidably receive the rod and the threaded head screwed into the bone.

The insertion of the nail components is performed using a tool coupled to the end of the component which has a handgrip for assisting the insertion and advancing movement of the nail inside the cavity.

The perforator used in these surgical operations has a perforation end shaped so as to remove bone during the rotational advancing movement.

Although advantageous in various respects, the telescopic nails of the prior art have drawbacks associated with insertion of the nail once the cavity has been formed.

In fact, although the surgeon may use a wire guide to accompany the insertion of the nail, since the wire guide has a small cross-section compared to the cavity, it may easily happen, when the perforator is removed, that the bone stumps become misaligned during the osteotomy operations. A misalignment of the bone complicates the procedure for insertion of the nail with the consequent risk of adversely affecting the implant and the successful outcome of the treatment.

Moreover, the nail insertion procedure according to the prior art is complex owing to the high number and size of the tools which the surgeon must use.

From the above there therefore arises the need to develop a telescopic nail and a tool which are able to reduce the complexity of the surgical procedure and minimize the possibility of misalignment of the bone stumps.

An object of the invention is to solve the problems of the prior art.

A particular object of the present invention is to devise a telescopic nail and a perforating tool which allow the limb to remain aligned during insertion of the nail into the cavity, ensuring the correct insertion of the nail.

A further particular object of the present invention is to devise a telescopic nail which ensures a high degree of fixing stability of the ends to the bone epiphyses and which at the same time does not hinder the correct bone growth.

A further particular object of the present invention is to devise a telescopic nail and a perforating tool which are able to reduce the complexity of the surgical implant method and the number and the size of the tools needed for the implant.

SUMMARY OF THE INVENTION

The aforementioned objects are achieved by a nail according to the present invention, of the type comprising a telescopic nail for the treatment of fractures or deformations of long bones, as for example in the case of osteogenesis imperfecta or pseudo-arthrosis. comprising:

- a hollow stem;
- a rod telescopically inserted into said hollow stem;
- a first fastening element coupled to one end of said hollow stem (2) for fixing to a first long bone end;
- a second fastening element coupled to an end of said rod for fixing to a second long bone end;
- an opposite end of said hollow stem being provided with a threaded coupling for coupling to an end of a tool which can be inserted into a cavity formed in the bone for insertion of the nail;
- said first fastening element is structured as a screw with a shank to be coupled to said one end of said hollow stem and a fixing head for fixing to the bone.

The basic idea of the present invention is in short that of providing a hollow stem of the telescopic nail which can be coupled to an end of a tool which can be inserted into a cavity formed in the bone for insertion of the nail itself.

In this way in fact it is possible to insert the hollow stem inside the cavity by advancing the tool and drawing along with it the said hollow stem.

Advantageously, this tool may be a perforating tool used to form the cavity for inserting the nail.

Once the hollow stem has been inserted into the cavity, the rod may be inserted into the hollow stem and the two components fixed to the bone by means of the associated fastening elements. In particular, the first fastening element may be coupled to the end of the hollow stem and then fixed to the corresponding end of the bone.

Preferably, the second fastening element is formed as one piece with the rod, even though alternatively they may be two separate parts which are then fixed together, for example by means of welding.

Advantageously, the coupling means may be present at both the ends of the hollow stem so that the surgeon does not have to worry about the direction of insertion of the hollow stem.

Moreover, preferably, the rod has a circular cross-section and is inserted inside a tubular stem. In other words, a telescopic coupling with a cylindrical profile is formed, this ensuring a high contact length, while limiting the friction and therefore the risk of jamming during the relative movement of the components, even in the event of bending and twisting of the nail during the treatment.

Preferably, the coupling means form a threaded coupling with the end of the tool.

In particular, the coupling means may consist of an internally threaded end of the stem for receiving, by means of screwing, an external thread of a coupling end of the tool.

The first fastening element may advantageously consist of a first screw comprising a first shank suitable for coupling with an end of the hollow stem and a fixing head for fixing to the bone.

The first shank may comprise an external thread designed to be screwed into the internally threaded end of the hollow stem, locking by means of plastic deformation the hollow stem in the engaged position of the thread.

Moreover, advantageously, the fixing head may comprise a threaded head portion suitable for being gripped within the bone; the threaded head portion having a conical profile with a taper angle of 145°±20% and height of 3 mm±20%.

Also, or only, the second fixing element may comprise a fixing head designed to be fixed to the bone.

This fixing head may advantageously comprise a threaded head portion suitable for being gripped within the bone; the threaded head portion having a conical profile with a taper angle of 145°±20% and/or height of 3 mm±20%.

The taper and height values of the threaded head portion define a pronounced conical form, which allows gripping to be achieved in a smaller bone thickness than in the prior art in such a way as not to penetrate into the growth cartilage and at the same time ensure the stability of the implant during the treatment.

The fixing head may also comprise an internal movement cavity designed to be fixed to an end of an axial movement tool and at least a recessed seat designed to provide a form-fit coupling with an end of the manoeuvring tool, the recessed seat being formed on the outside of the internally threaded cavity so as to allow the simultaneous coupling of said axial movement tool and said manoeuvring tool.

The aforementioned objects are achieved by a perforating tool according to the present invention, of the type comprising a perforating end designed to form inside a long bone a cavity for the insertion of the telescopic nail.

Advantageously, the perforating tool comprises a coupling end, opposite to the perforating end, comprising counter-coupling means designed to be coupled with corresponding coupling means of an end of said hollow stem of a telescopic nail.

The aforementioned telescopic nail above may be advantageously implanted by means of an operating technique described hereinbelow.

Method for implanting a telescopic nail comprising the following steps:

- providing a telescopic nail comprising:
- a hollow stem;
- a rod inserted telescopically into the hollow stem;
- a first fastening element coupled to an end of the hollow stem for fixing to a first long bone end;
- a second fastening element coupled to an end of the rod for fixing to a second long bone end;
- one end of the hollow stem being provided with coupling means for coupling to an end of a tool which can be inserted into a cavity formed in the bone for insertion of the nail.
- preparing a tool which can be inserted inside a cavity formed in the bone for inserting the nail, comprising:

a coupling end comprising counter-coupling means designed to be coupled to the coupling means of an end of the hollow stem of the telescopic nail;

- inserting an end of the tool opposite to the coupling end inside the cavity through a first end of the bone;
- coupling the coupling means of a first end of the hollow stem of the telescopic nail together with the counter-coupling means of the coupling end of the tool;
- advancing the tool inside the cavity until it comes out completely from the other long bone end, drawing along with it the hollow stem into the cavity;
- uncoupling the tool from the hollow stem.

The further components of the nail may be then implanted by carrying out the following steps:

inserting the end of the rod of the telescopic nail, opposite to the second fastening element, into the hollow stem through the other end of the hollow stem, in particular before advancing the tool;

coupling the first fastening element to the first end of the hollow stem;

fixing the first fastening element to the second bone end;

fixing the second fastening element to the first bone end;

The aforementioned implant method allows the bone to kept aligned and ensures mechanical continuity inside the bone itself.

The tool may be advantageously a perforating tool comprising:

a perforating end designed to form the cavity for insertion of the telescopic nail;

a coupling end, opposite to the perforating end, comprising counter-coupling means designed to be coupled with corresponding coupling means of an end of the hollow stem of the telescopic nail.

In this case the cavity is formed during the insertion and advancing movement of the perforating tool inside the bone.

In this way a single tool may be used both to form the cavity and to insert the hollow stem of the nail into this cavity, thus reducing the complexity of the implant operation both in terms of number of tools used and steps performed, compared to the known techniques.

The step of coupling the coupling means with the counter-coupling means may also be performed before inserting the tool into the bone.

In particular, it is possible to use a tool having a smaller length than that of the long bone, to couple the hollow stem to the tool and to insert the tool using the same stem as an advancing guide. In other words, the stem acts as a tool.

In this way the costs for production of the said tool may be reduced.

The tool may also be supplied to the surgeon already coupled to the stem, allowing the number of operating steps to be further reduced.

Further characteristic features and advantages of the telescopic nail and the perforating tool according to the present invention will appear more clearly form the description, provided hereinbelow, of examples of embodiment provided by way of a non-limiting example.

BRIEF DESCRIPTION OF THE DRAWINGS

The present description makes reference to the attached drawings in which.

In the different figures, similar elements will be identified by similar reference numbers.

DETAILED DESCRIPTION OF PREFERRED EMBODIMENTS

Figures 1, 2:
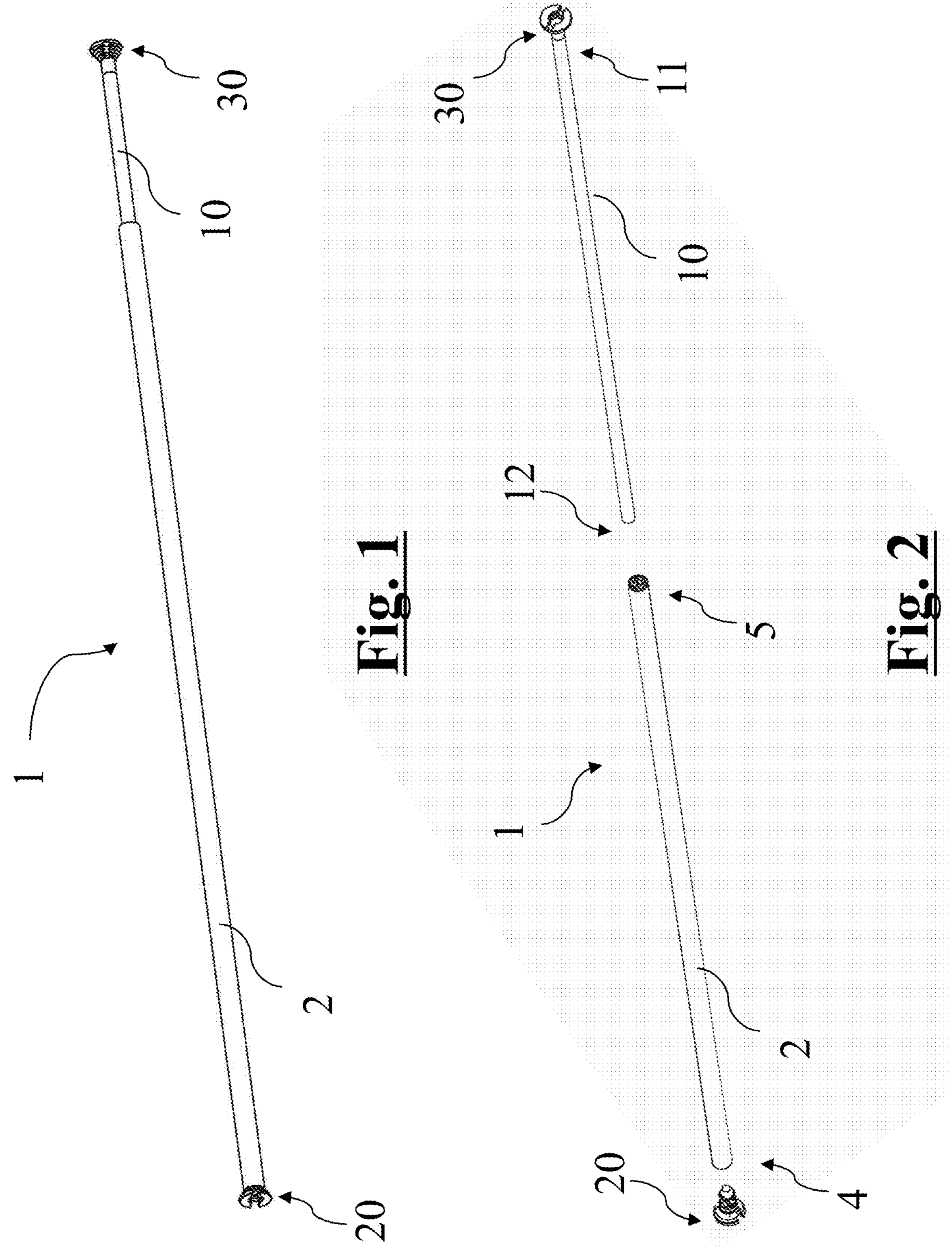
FIG. 1 shows a perspective and schematic view of an embodiment of a telescopic nail provided in the accordance with the present invention, in the assembled condition.
FIG. 2 shows a schematic perspective view of the telescopic nail according to FIG. 1, in the disassembled condition.
Figures 3, 4, 5:
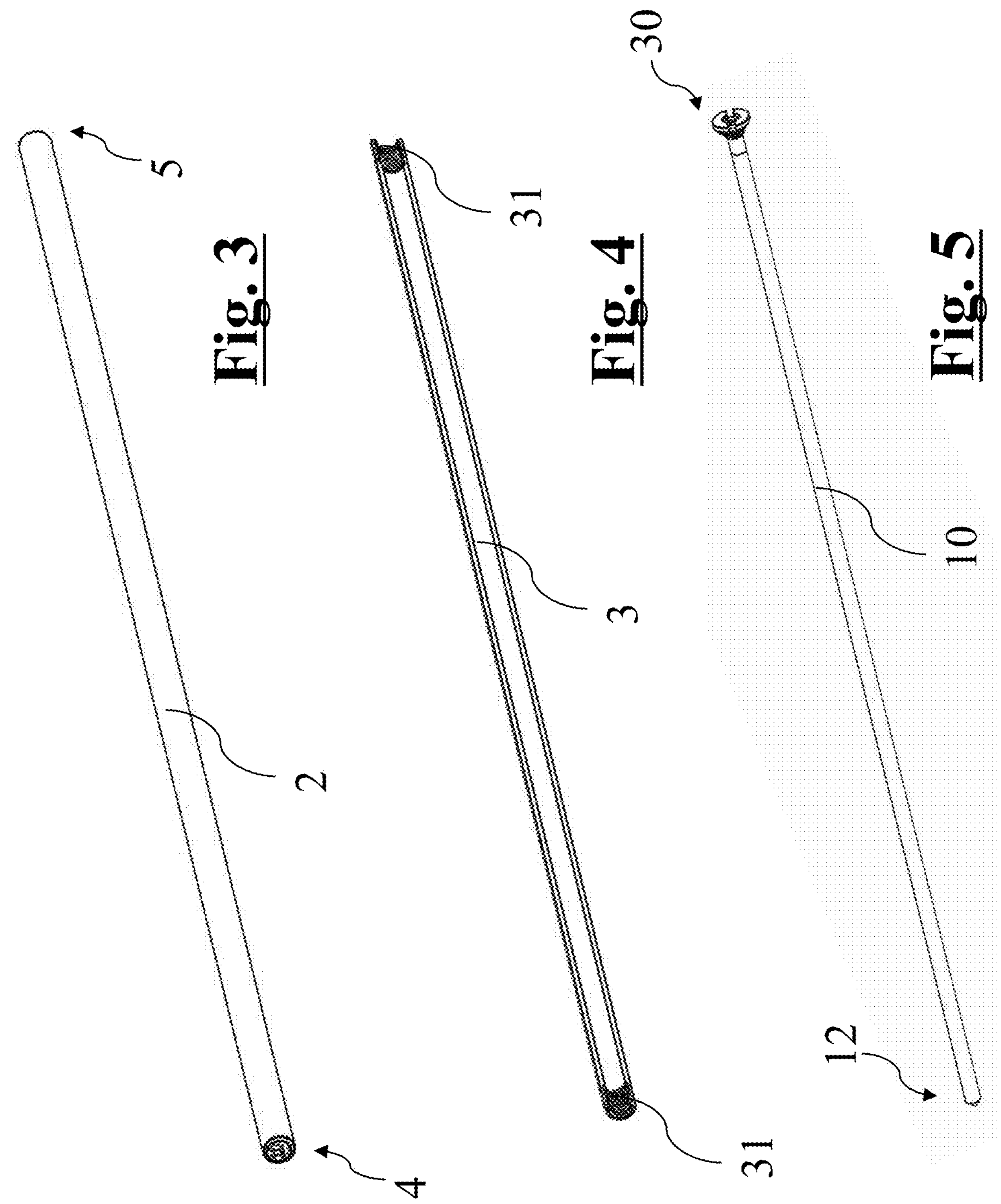
FIG. 3 shows a schematic perspective view of a hollow stem of the telescopic nail according to FIG. 1.
FIG. 4 shows a schematic perspective view of the hollow stem according to FIG. 3, cross-sectioned along a longitudinal plane.
FIG. 5 shows a schematic perspective view of a rod of the telescopic nail according to FIG. 1.

With reference to the attached figures, non-limiting explanatory embodiments of the telescopic nail and the perforating tool according to the present invention are described below.

The telescopic nail according to the invention is particularly suitable, albeit not exclusively, for the treatment of fractures or deformations of long bones, as for example in the case of osteogenesis imperfecta or pseudo-arthrosis, in particular in paediatric patients.

The telescopic nail 1 generally comprises a hollow stem 2 and a rod 10 which can be slidably inserted inside an internal cavity 3 of the stem 2, thus forming a telescopic coupling.

In the explanatory embodiments, this telescopic coupling has a cylindrical shape, namely the rod has a circular cross-section and is inserted inside a tubular stem with a slightly larger diameter.

This type of profile has been envisaged since it has the advantage of ensuring a high contact area which limits the friction during the relative sliding of the components 2, 10 also during any bending and twisting of the nail during the treatment. Other types of profile, such as splined profiles, which are used in the sector are instead prone to seizing.

The telescopic nail 1 also has a first fastening element 20 designed to be removably fixed to one of the first and second stems ends 4, 5 and in turn to fix the hollow stem 2 to an end of the bone.

Figures 10, 11:
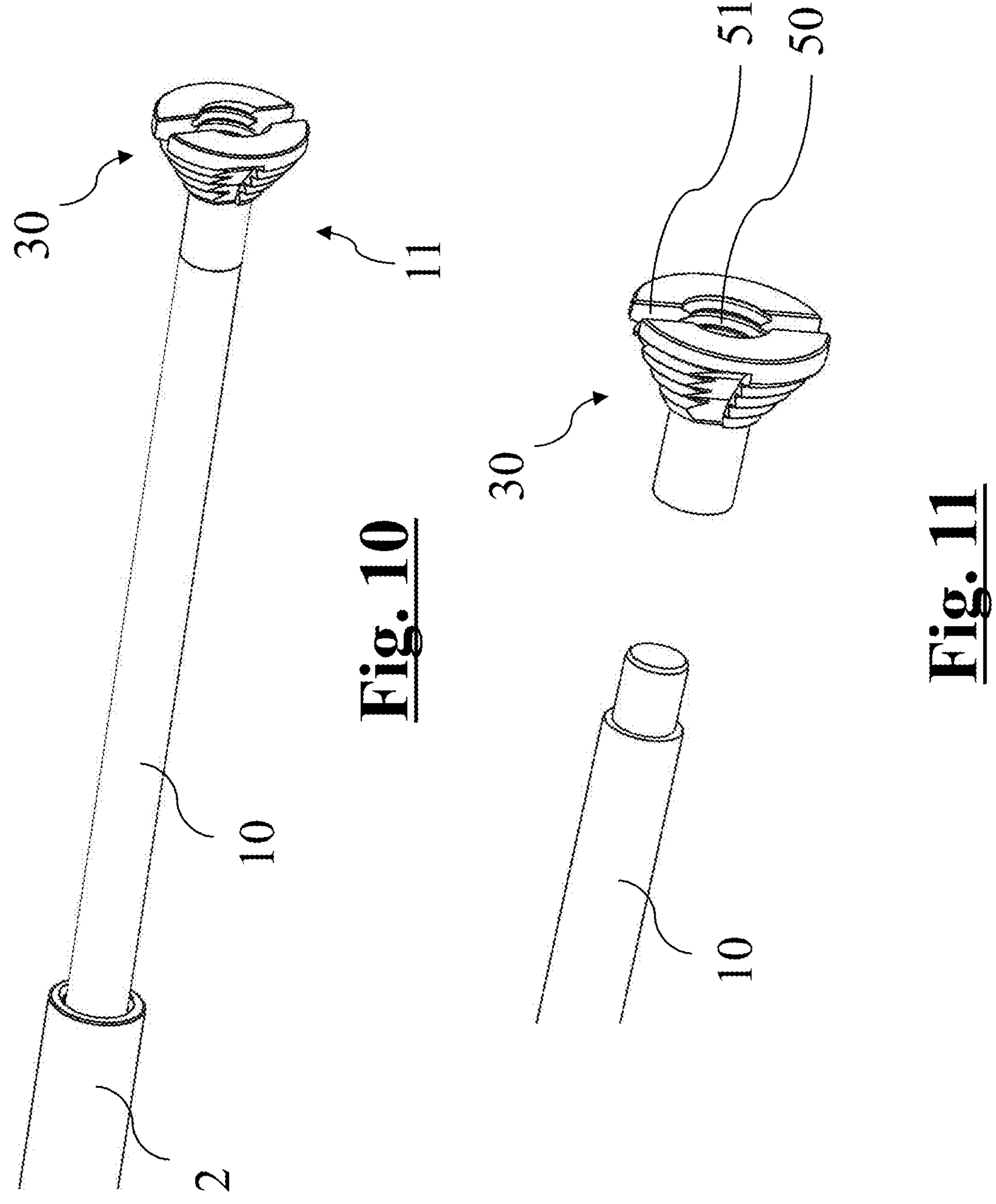
FIG. 10 shows a schematic perspective view of a detail of the telescopic nail according to FIG. 1.
FIG. 11 shows a schematic perspective view of a detail of the telescopic nail with an alternative embodiment of the second fastening element.
Figure 12:
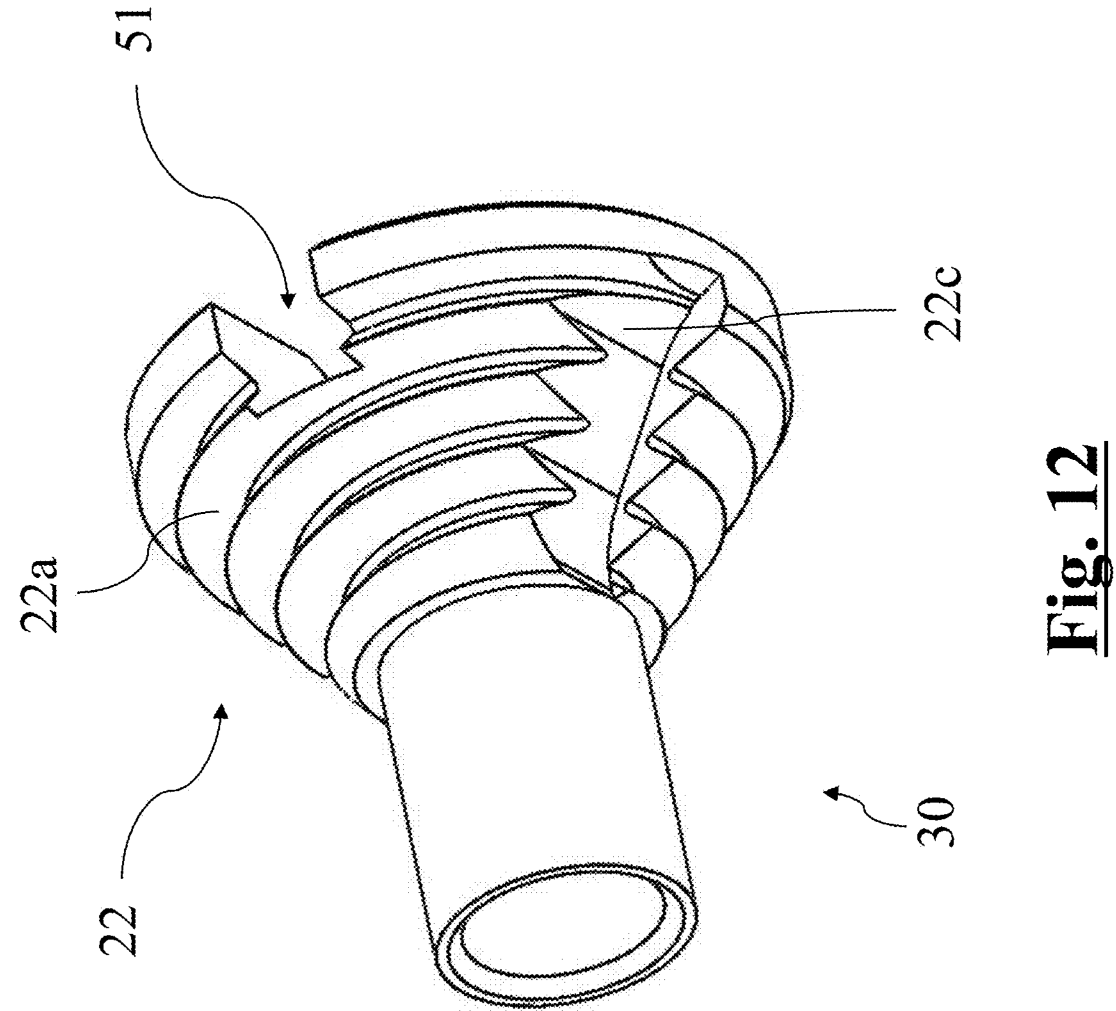
FIG. 12 shows a schematic perspective view of a detail of the second fastening element according to FIG. 11.

A second fastening element 30 is placed at a first rod end 11 and is designed to fix the rod 10 to an opposite end of the bone. This second fastening element 30 is preferably formed as one piece with the rod 10, but may be made separately and then fixed to the end 11 of the rod 10 (see FIGS. 10, 11) for example by means of welding.

As will be explained more fully in the continuation of the description, the hollow stem 2 has at the first stem end 4 coupling means 40 designed to be coupled to corresponding counter-coupling means 540 of a perforating tool 500.

In the preferred embodiments described here, these coupling means 40 are present also at the second stem end 5 and consist of an internal thread 31 formed inside the internal cavity 3.

The first fastening element 20 consists instead of a first screw comprising a fixing head 22 designed to be fixed to the bone and a first shank 21 designed to be coupled with a stem end 4, 5.

In particular, the first shank 21 comprises an external thread **21*a* complementing the internal thread 31 of the stem end 4, 5. This first shank 21 may also terminate in a conical engaging portion 21*b* for facilitating centring of the screw during insertion inside the internal cavity 3 of the stem 2 and subsequent engagement with the internal thread 31**.

The fixing head 22 also has a threaded head portion **22*a*** having a conical shape, or rather frustoconical shape, with a taper angle $\alpha$, defined as being the angle between the stem and the conical surface, and a height H.

The thread of the threaded portion **22*a* may be interrupted by an anti-screwing groove 22*c*** provided so as to increase the stability of fixing to the bone.

Advantageously, the threaded head portion **22*a*** has a pronounced conical form so as to ensure a firm grip in a small bone thickness. Differently from the threaded ends of the nails according to the prior art, which have extensive threads penetrating into the growth cartilage, this pronounced conical form allows stable fixing to be obtained with a thread having a small length so as not to interfere with the growth cartilage.

In particular, the pronounced conical form is defined by a taper angle $\alpha$ of 145°±20% and a height H of 3 mm±20%. More preferably, $\alpha$ is equal to 145°±10% and His equal to 3 mm±10%. Even more preferably, $\alpha$ is equal to 145° and H is equal to 3 mm.

Figure 20:
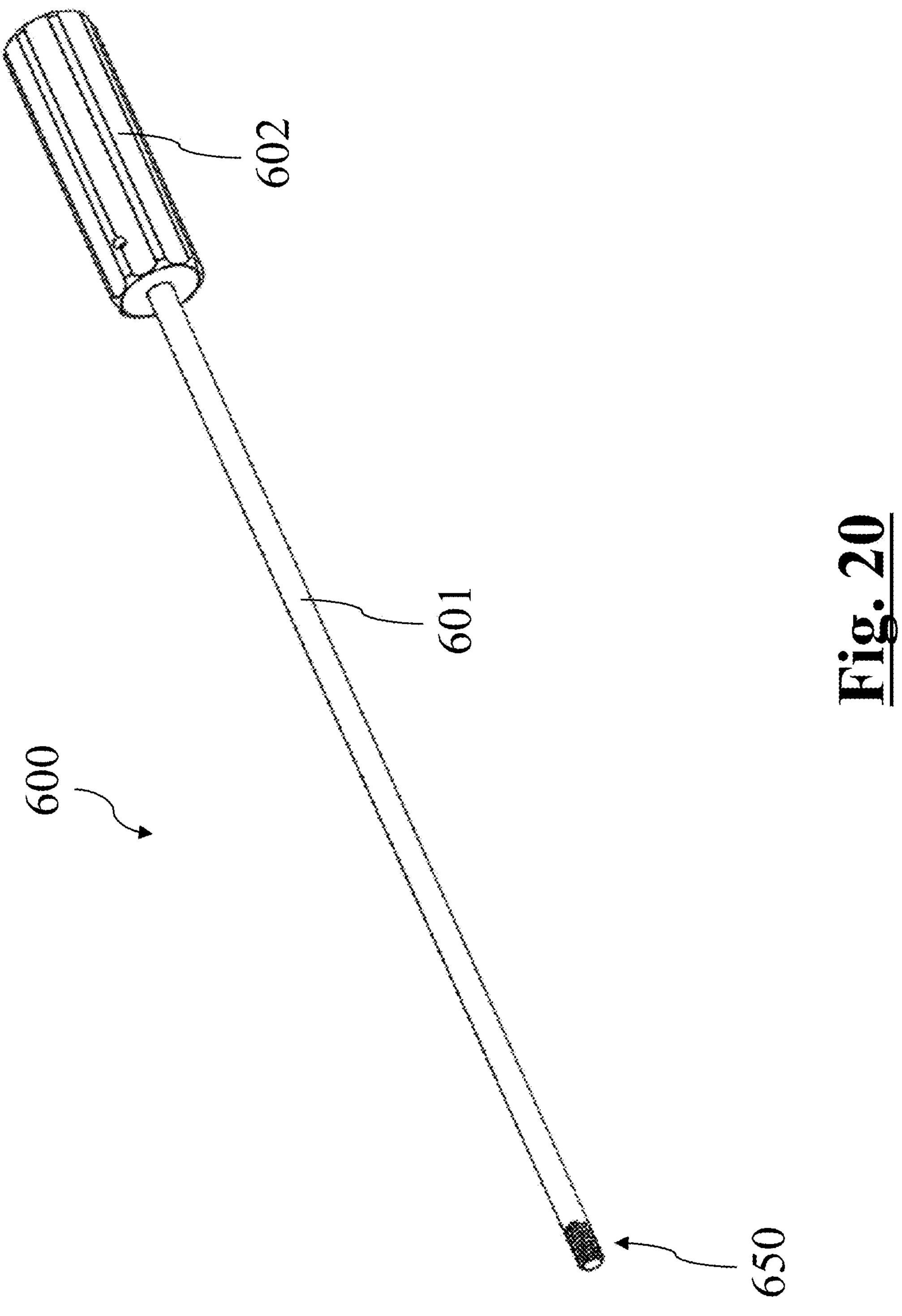
FIG. 20 shows a schematic perspective view of an axial movement tool which can be coupled to the first and/or second fastening element of the telescopic nail according to FIG. 1.

The fixing head 22 may also have an internally threaded cavity 50 accessible from the outside via the top surface 23 of the fixing head 22. A corresponding threaded end 650 of an axial movement tool 600, such as for example that shown in FIG. 20, can be inserted by means of screwing inside the internally threaded cavity 50. As can be seen from this figure, the threaded end 650 is in particular located at the apex of a movement bar 601 which has at the opposite end to the threaded end a movement handgrip 602.

Figures 7, 8:
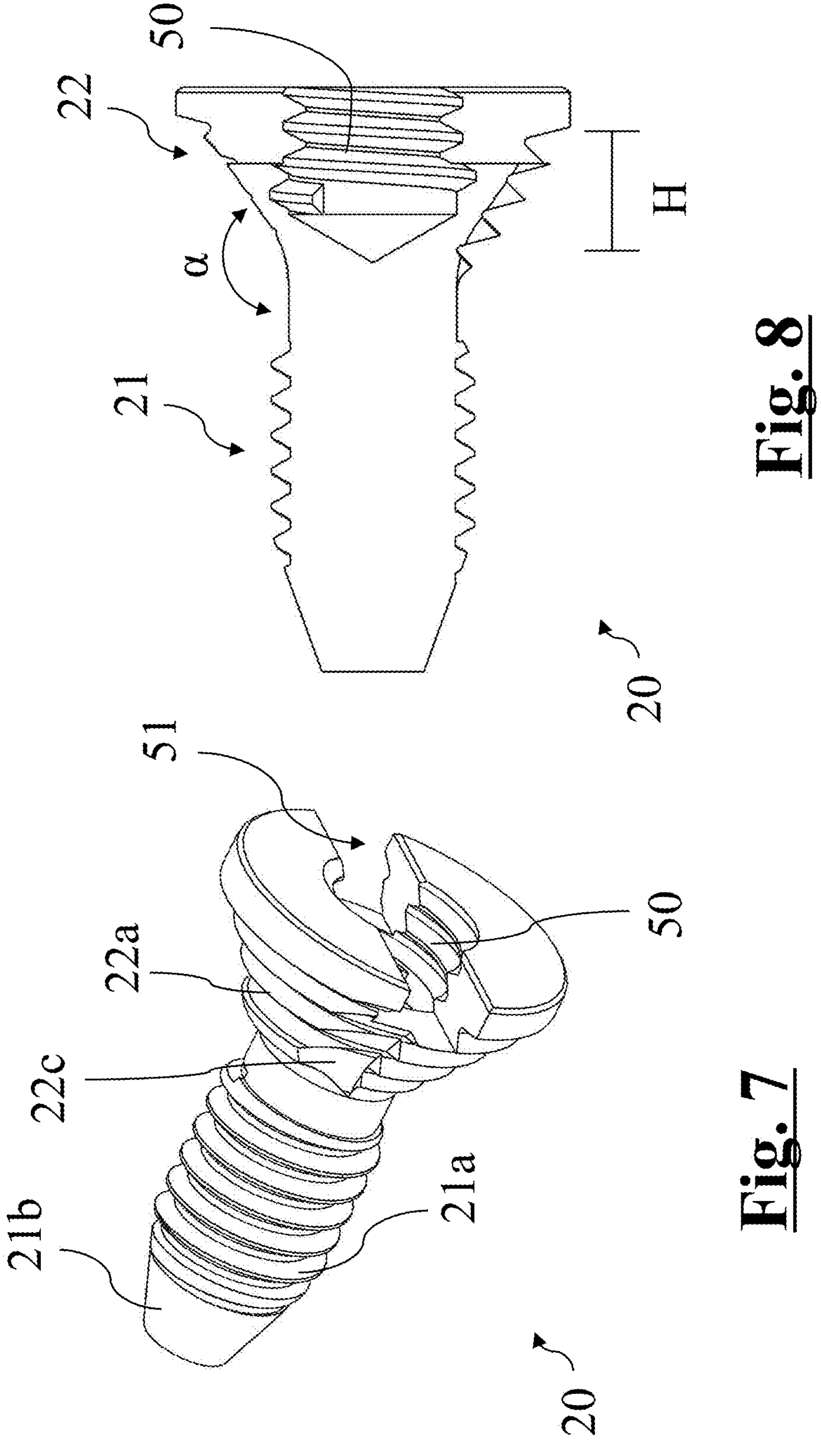
FIG. 7 shows a schematic perspective view of a first fastening element of the telescopic nail according to FIG. 2.
FIG. 8 shows a longitudinal section through the first fastening element according to FIG. 7.

The thread of the cavity 50 is cylindrical as shown in FIG. 8. A chamfer for facilitating the introduction of the tool may also be present.

Figures 18, 19:
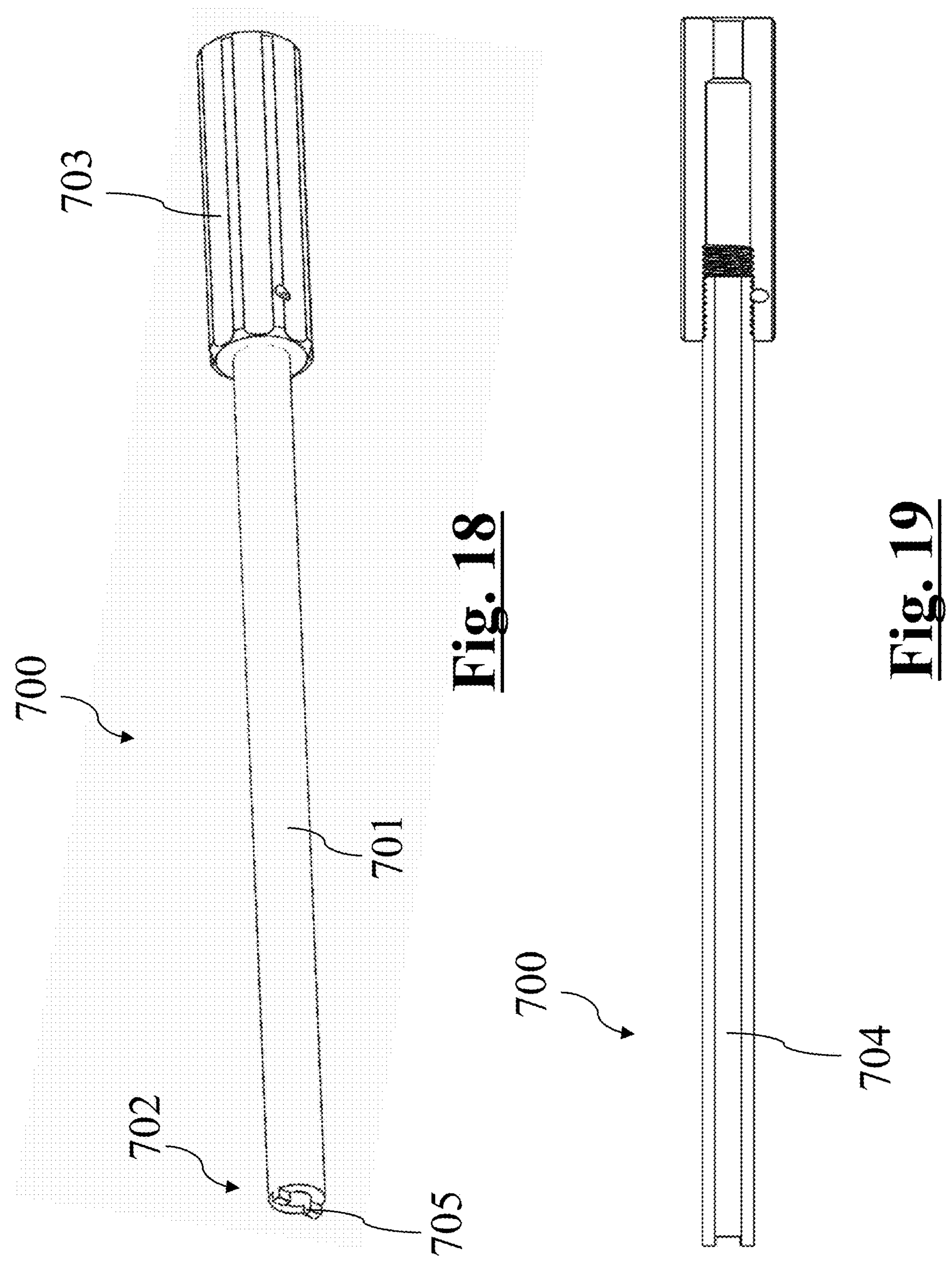
FIG. 18 shows a schematic perspective view of a tightening tool which can be used to screw the first and/or second fastening element of the telescopic nail according to FIG. 1.
FIG. 19 shows a cross-section along a longitudinal plane of the tool according to FIG. 18.

A recessed seat 51, 51' shaped so as to provide a form-fit coupling with an end of the manoeuvring tool 700, such as that for example shown in FIGS. 18 and 19, is also formed in the top surface 23. The recessed seat 51, 51' is advantageously formed on the outside of the internally threaded cavity 50 so as to leave free access to the internally threaded cavity 50 and allow the simultaneous coupling of the manoeuvring tool 700 with the recessed seat 51 and of the axial movement tool 600 with the internally threaded cavity 50.

The manoeuvring tool 700 may comprise a manoeuvring bar 701 having a manoeuvring end 702 shaped so as to provide a form-fit coupling with the recessed seat 51 and an opposite manoeuvring handgrip 703. This manoeuvring tool 700 is advantageously cannulated, namely has a guide cavity 704 which extends over the whole length of the tool and inside which the movement bar 601 of the axial movement tool 600 can be inserted in a freely rotatable and displaceable manner.

Figure 6:
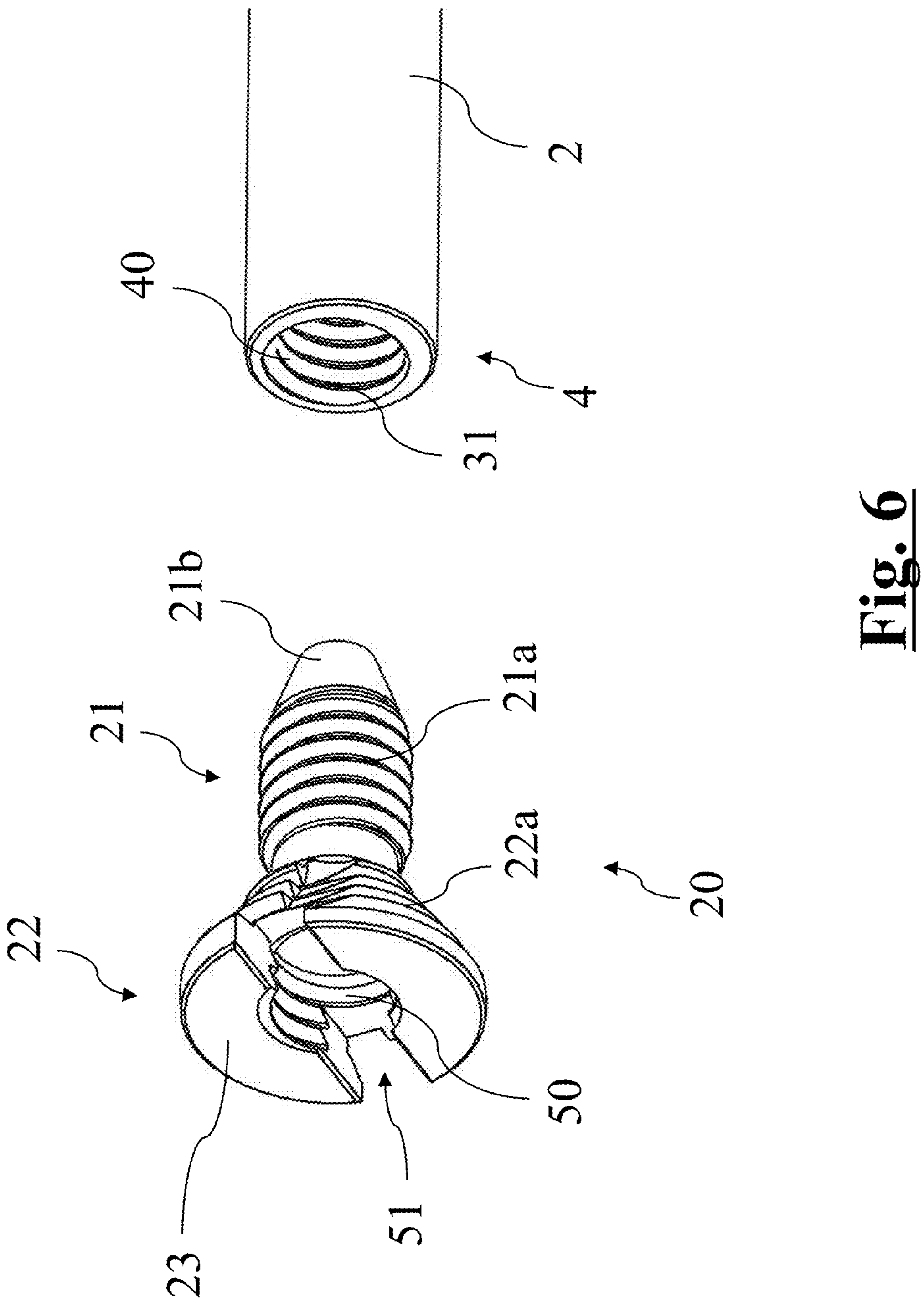
FIG. 6 shows a schematic perspective view of a detail of the telescopic nail according to FIG. 2.

In particular, the recessed seat 51 may have a transverse groove which extends outside of the internally threaded cavity in opposite radial directions with respect to the longitudinal axis of the screw (see FIGS. 6 and 7).

The example a manoeuvring tool 700 shown in FIG. 18 has a manoeuvring end 702 with manoeuvring teeth 705 which are aligned and located in a diametrically opposite position with respect to the longitudinal axis of the cavity and can be engaged inside the recessed seat 51 in order to transmit a screwing torque.

Figure 9:
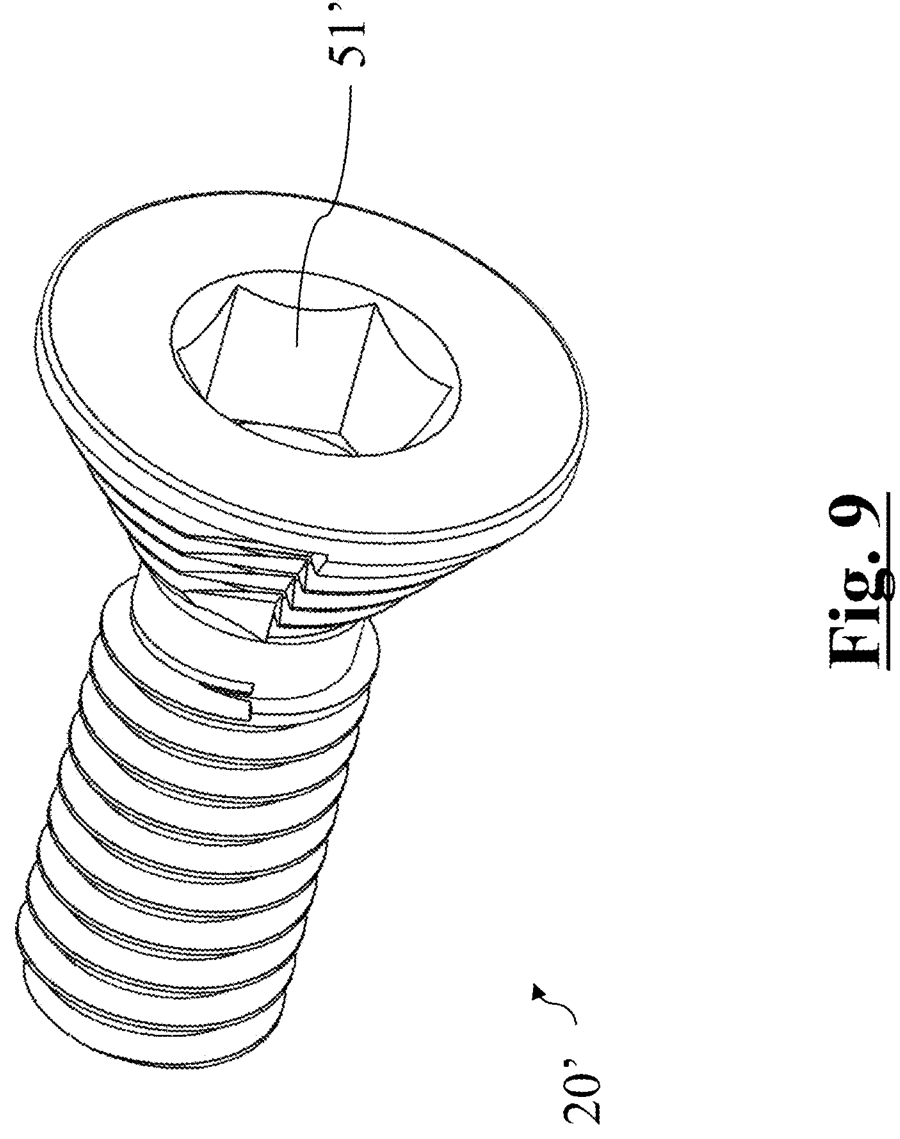
FIG. 9 shows a schematic perspective view of an alternative embodiment of the first fastening element.

FIG. 9 shows an alternative embodiment of the first fastening element 20' which differs in that it has an almost entirely threaded shank and a recessed seat 51', suitable for an Allen key, formed above the internally threaded cavity 50. A manoeuvring end which instead of the manoeuvring teeth has a hexagonal-profile tip crossed by the guide cavity may be used for insertion inside the recessed seat 51' in order to transmit a tightening torque to the screw.

The second fastening element 30 preferably also has a fixing head 22 such as that described above in connection with the first fastening element 20.

Figure 21:
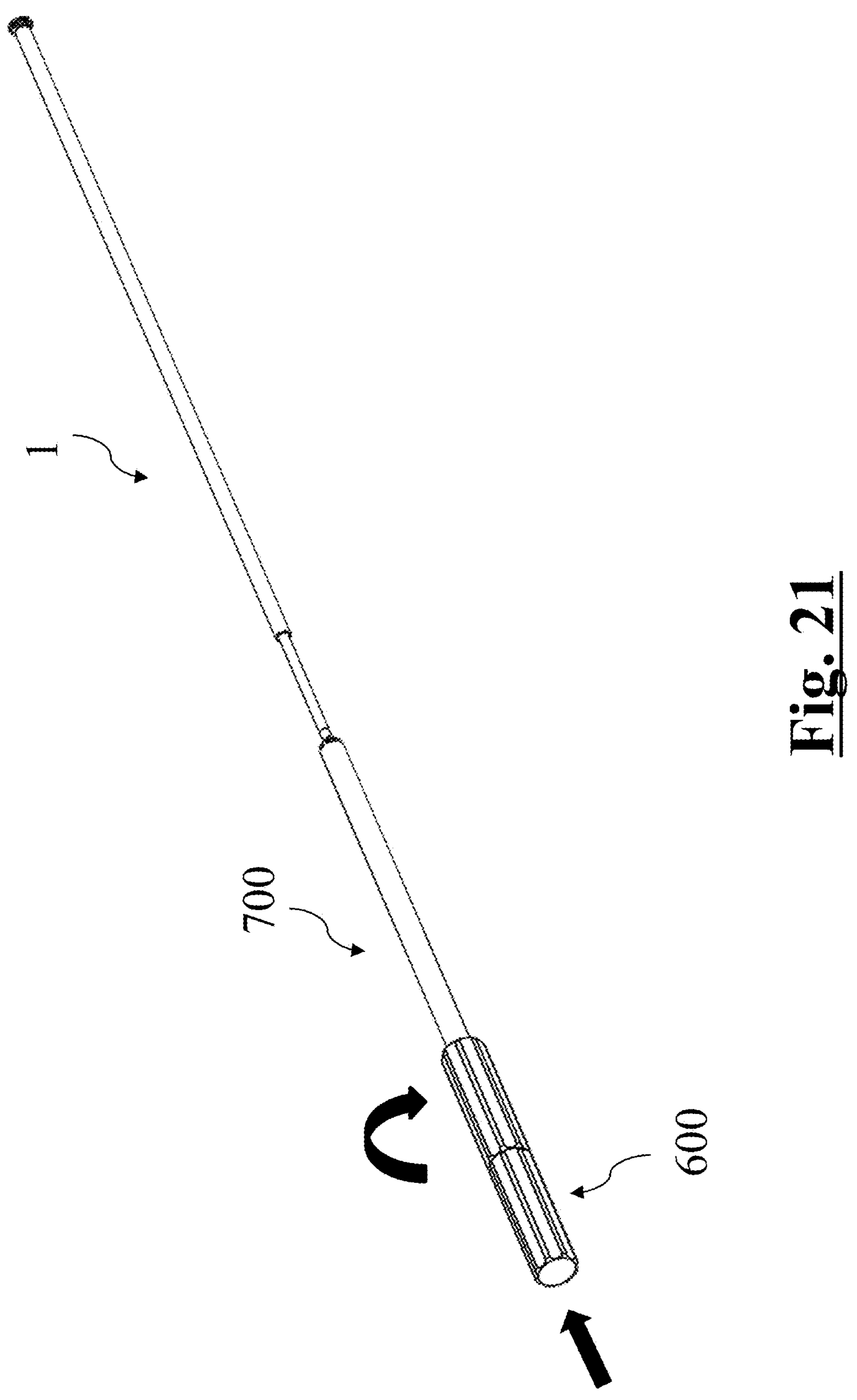
FIG. 21 shows a schematic perspective view of a system comprising the tools according to FIGS. 18 and 20 coupled to the telescopic nail according to FIG. 1.
Figure 22:
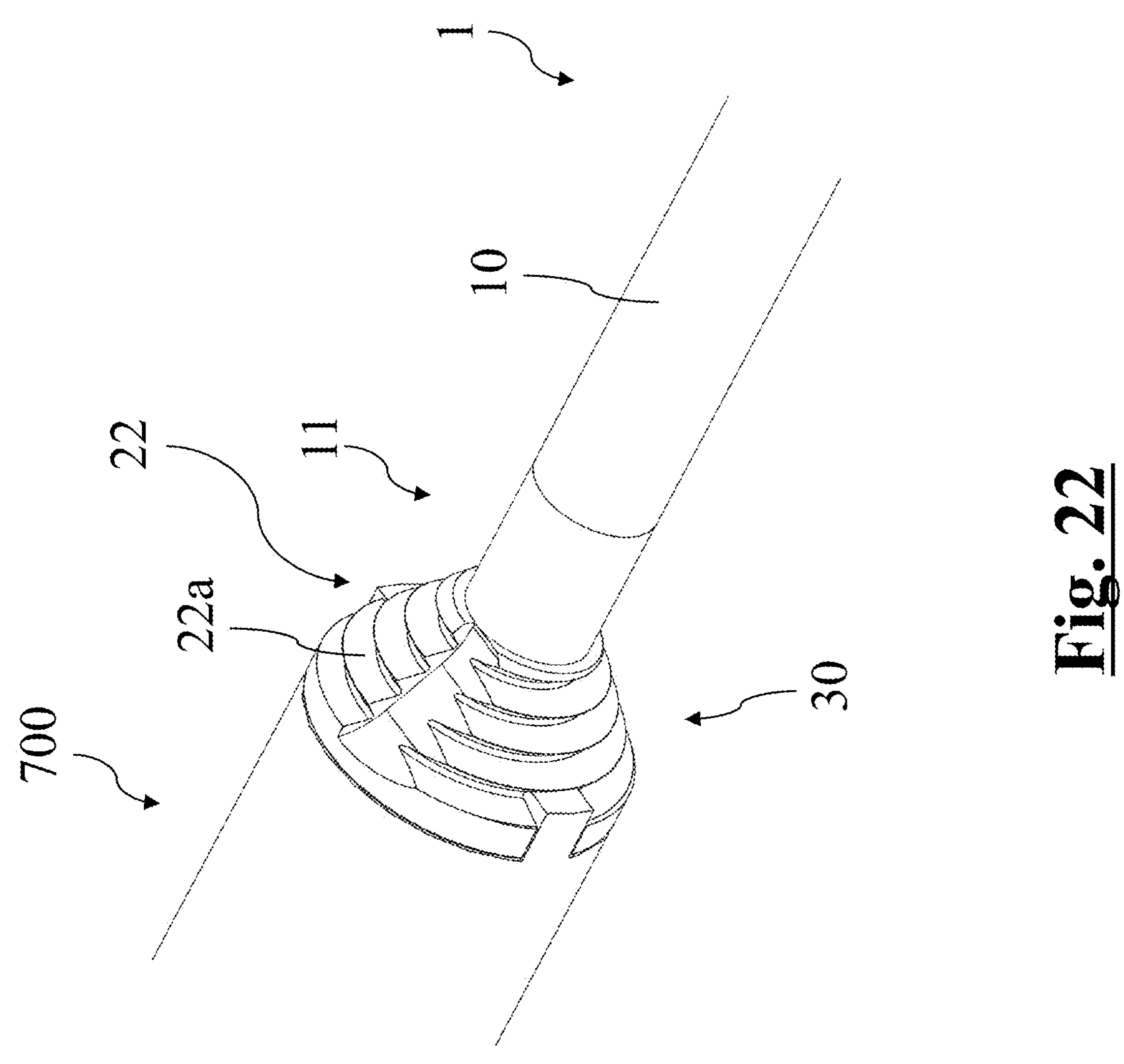
FIG. 22 shows a detail of FIG. 21.
Figures 23, 24:
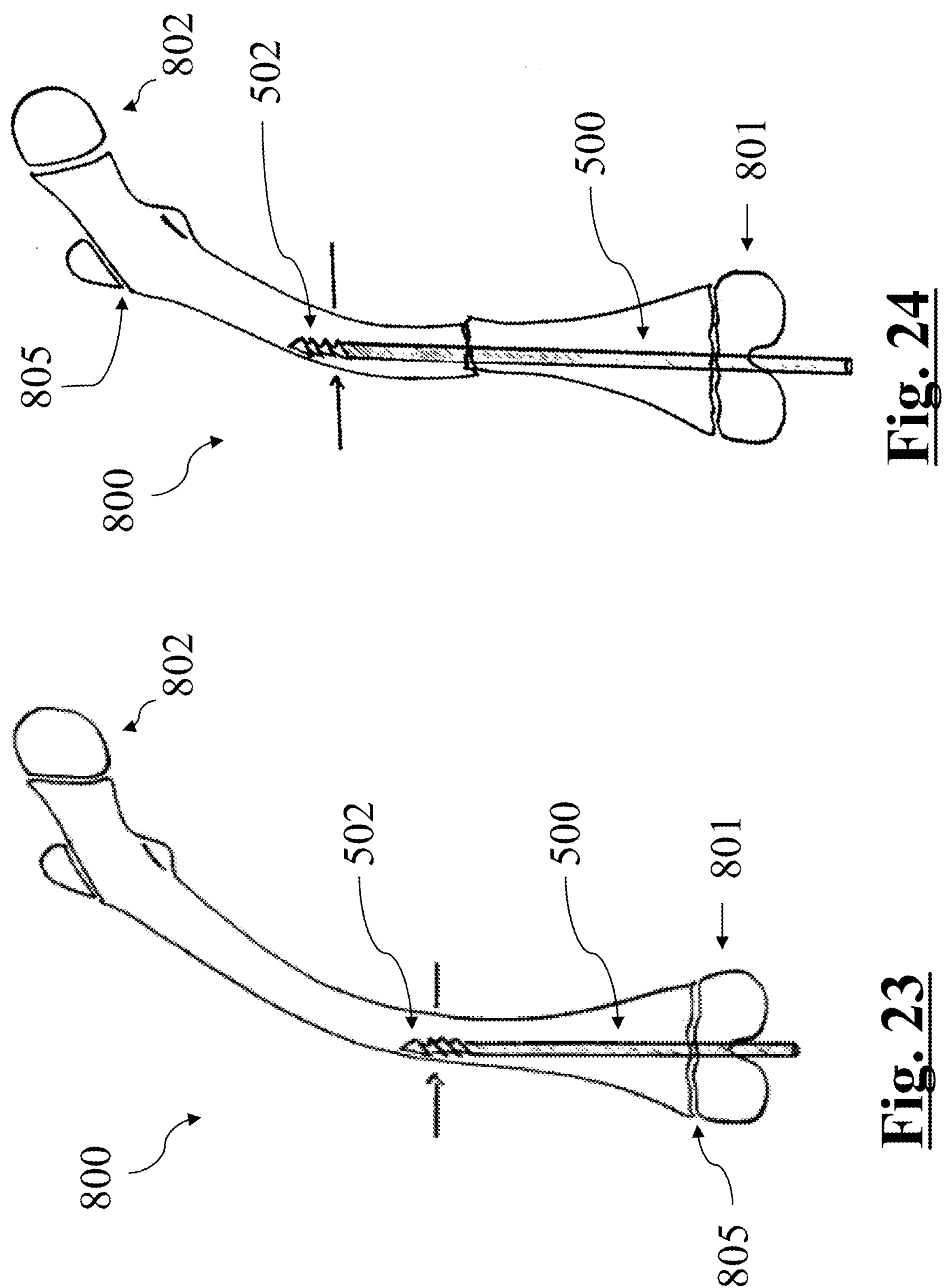
FIG. 23 shows the perforating tool according to the invention during the start of the step for forming the cavity for inserting the telescopic nail inside a deformed thigh-bone.
FIG. 24 shows the perforating tool according to FIG. 23 being advanced along the bone after the execution of a first osteotomy.

The assembly consisting of the axial movement tool 600 inserted inside the manoeuvring tool 700 may therefore be coupled with the fixing head 22 of the first or second fastening element 20, 30 (see FIG. 21) and be used to perform a series of operations.

In particular, once the second fastening element 30 has been stabilized by screwing the threaded end 650 of the movement bar 601 into the internally threaded cavity 51 the rod 10 of the telescopic nail 1 may be inserted into the bone, the second fastening element 30 screwed into the bone after inserting the manoeuvring end 702 into the recessed seat 51, and if necessary extraction or insertion of the nail performed by means of the movement tool 600, for example during removal of the nail.

The aforementioned assembly may also be used to guide the insertion and screw the shank 21 of the first fastening element 20 into a stem end 4, 5 and, once stabilized, to guide the movements of the stem 2 and screw the first fastening element 20 into the bone.

With reference to FIGS. 13-17, explanatory non-limiting embodiments of the perforating tool 500, 500' will now be described.

Differently from the perforating tools according to the prior art, the perforating tool 500, 500' according to the present invention comprises a coupling end 501, opposite to a perforating end 502, shaped so as to remove bone tissue during the formation of the nail insertion cavity and comprising counter-coupling means 540 designed to be coupled to the coupling means 40 of a stem end 4, 5 of the hollow stem 2 of the telescopic nail 1.

The perforating tool 500, 500' comprises in particular a guide bar 503 extending between the coupling end 501 and the perforating end 502, the latter have a shape known per se.

Figures 13, 14:
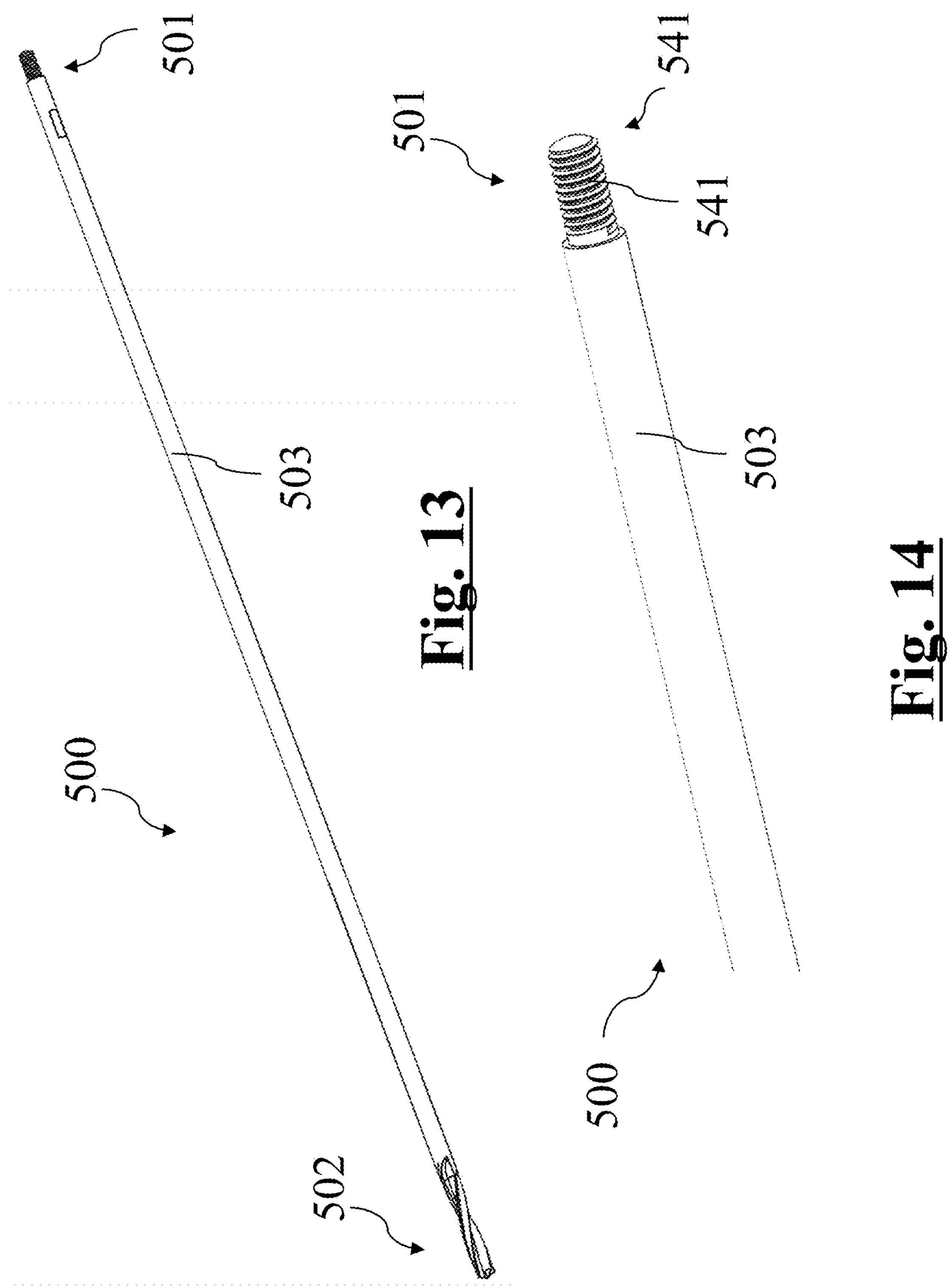
FIG. 13 shows a schematic perspective view of a first embodiment of a perforating tool provided in the accordance with the present invention.
FIG. 14 shows a schematic perspective view of the coupling end of the tool according to FIG. 13.

In the embodiment shown in FIG. 14, the counter-coupling means 540 consist of an end-piece provided with an external thread 541 which can be fixed by means of screwing inside the internal thread 31 of one of the stem ends 4, 5.

Alternative embodiments may envisage different types of coupling means and counter-coupling means.

Figures 25, 26:
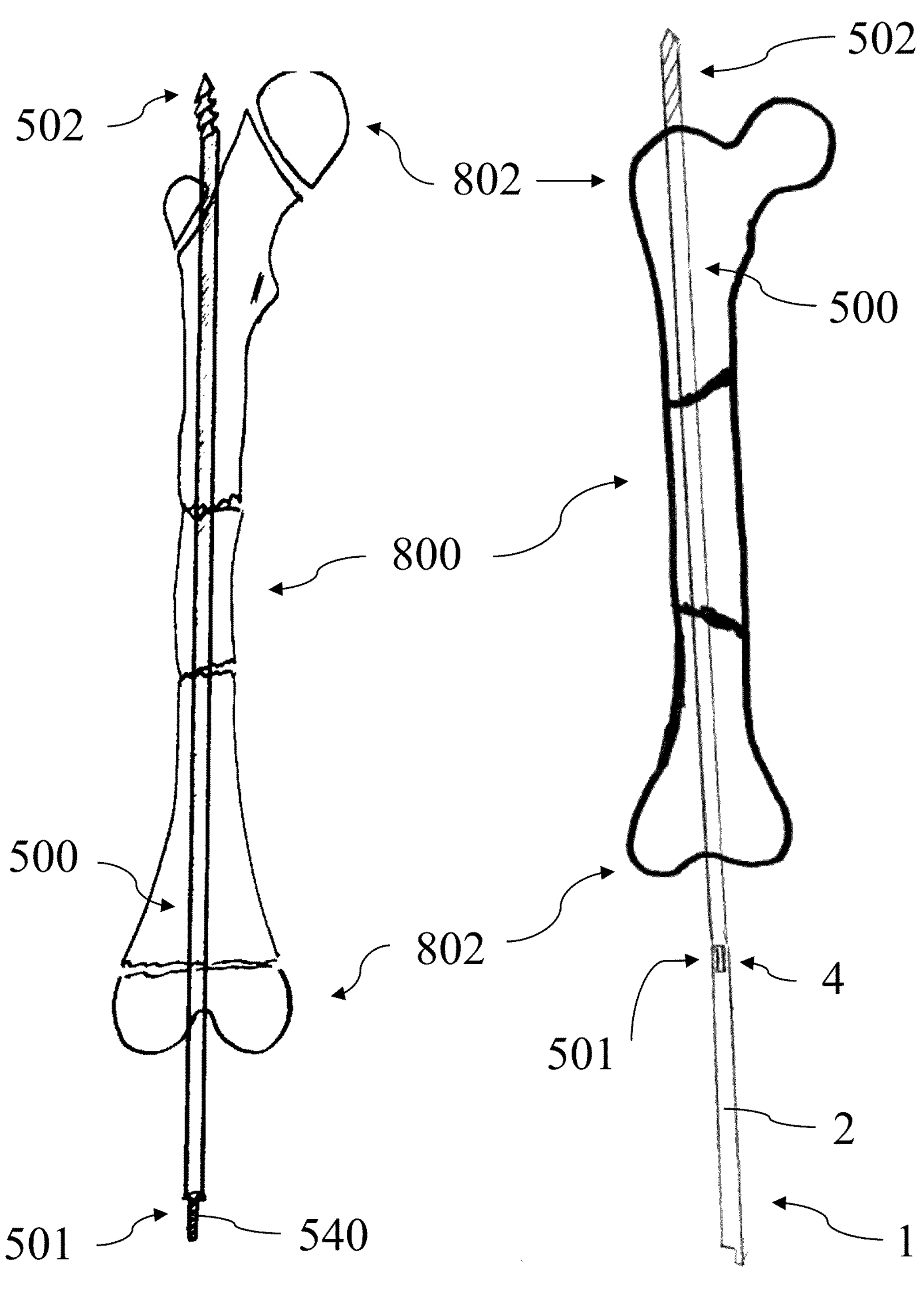
FIG. 25 shows the perforating tool completely inserted inside the thigh-bone.
FIG. 26 shows the perforating tool according to FIG. 25 with, coupled thereto, the hollow stem of the telescopic nail according to the invention.

FIGS. 13 and 25 show a first embodiment of the perforating tool 500 which has a length greater than the long bone inside which it must be inserted.

A second embodiment of the perforating tool 500', shown in FIGS. 15 and 16, may advantageously have a smaller length than that of the long bone inside which it must be inserted, so as to simplify the implant operations and reduce the instruments needed to perform such an implant, as will emerge more clearly below.

Both the perforating tool 500, 500' and the hollow stem 2 of the telescopic nail 1 may have lateral milled zones 70 which allow the perforating tool to be stabilized on and removed from the said nail.

The telescopic nail 1 may be advantageously implanted in the long bone of a patient in a secure and effective manner compared to the nails of the prior art owing to the use of the perforating tool according to the invention.

For explanatory purposes, with reference to FIGS. 23-28, a method for implanting the telescopic nail 1 in a deformed thigh-bone 800, which uses the perforating tool 500, is described below.

Firstly, the perforating end 501 of the perforating tool 500 is inserted into the distal end 801 of the thigh-bone 800 and the perforating tool 500 is gradually advanced so as to form an internal cavity for inserting the telescopic nail 1. At the same time osteotomies may be carried out for alignment of the bone.

The perforating tool 500 is advanced until the perforating end 502 emerges from the proximal end 802 of the bone, leaving the coupling end 502 outside of the distal end 801 of the bone (FIG. 25).

The second rod end 12 of the rod 10, opposite to the second fastening element 30, is inserted into the internal cavity 3 of the hollow stem 2 by means of the second stem end 5.

The first stem end 4 of the hollow stem 2 of the telescopic nail 1 is coupled by means of screwing to the coupling end 502 of the perforating tool 500 (FIG. 26) and the perforating tool 500 extracted from the proximal end 801 of the bone, being drawn along behind the hollow stem 2 until the first stem end 4 emerges form the proximal end 802 of the bone.

During this latter step, the rod 10 is kept inserted inside the internal cavity 3 of the hollow stem 2, ensuring structural continuity.

The perforating tool 500 is then uncoupled from the hollow stem 2.

The threaded head portion 22*a* of the second fastening element 30 is fixed inside the distal end of the bone.

The external thread 21*a* of the first fastening element 20 is fixed inside the internal thread 41 of the first rod end 4 and then the threaded head portion 22*a* of the first fastening element 20 is fixed inside the proximal end 802 of the bone.

Figures 27, 28:
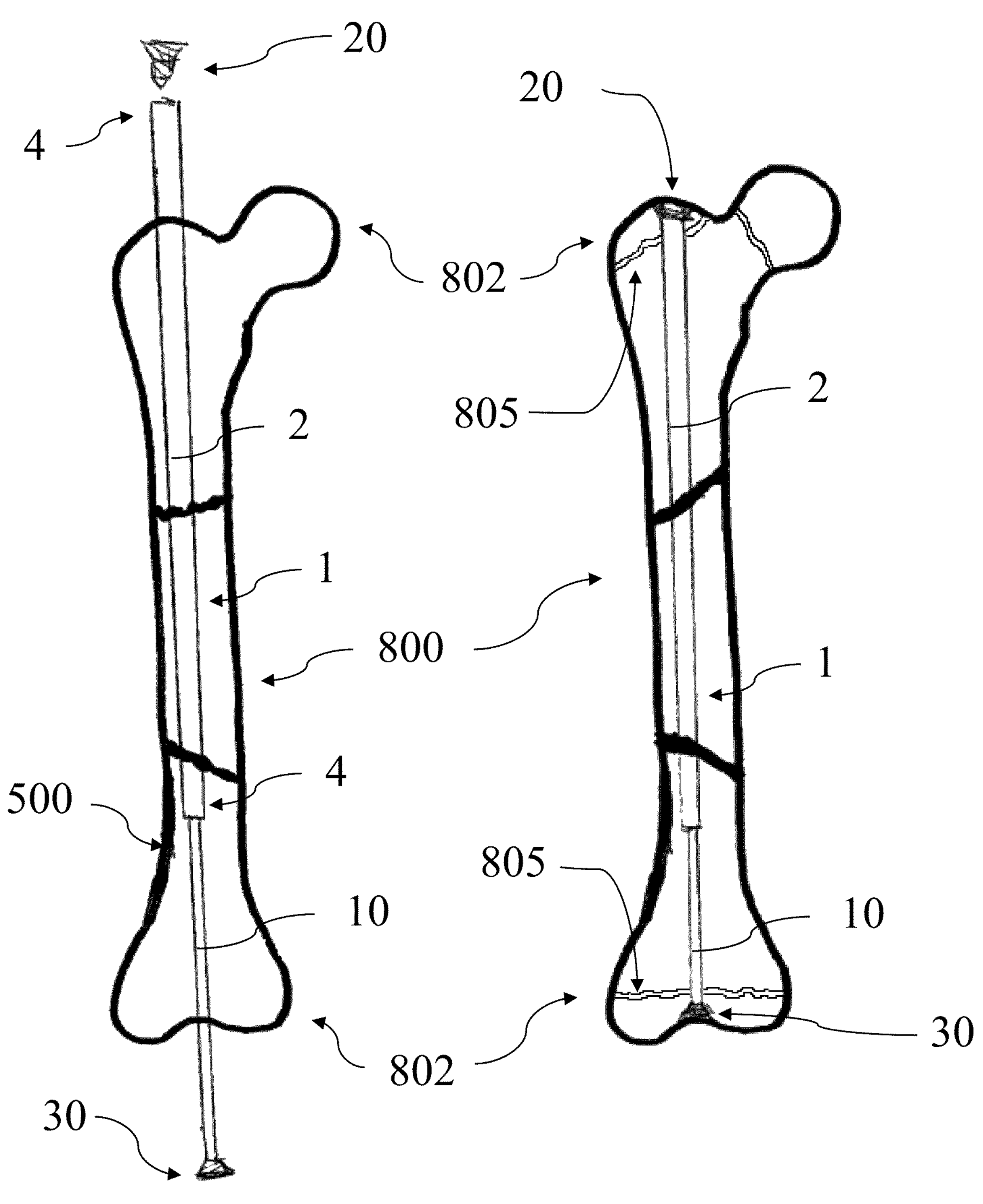
FIG. 27 shows a telescopic nail according to the invention partially inserted inside the thigh-bone with the fastening elements not fixed.
FIG. 28 shows the telescopic nail according to FIG. 27 completely inserted inside the thigh-bone with the fastening elements fixed to the bone.

As discussed above, the pronounced conical form of the threaded head portion 22*a* of the fastening elements 20, 30 allows them to be inserted inside the bone end without affecting the growth cartilage 805 (see FIG. 28).

Moreover, the operations for inserting the rod 10, the fixing of the fastening elements 20, 30 inside the bone and the tightening of the first fastening element 20 together with the first stem end 4 may be carried with the assembly consisting of manoeuvring tool and movement tool 600 described above.

Figures 15, 16:
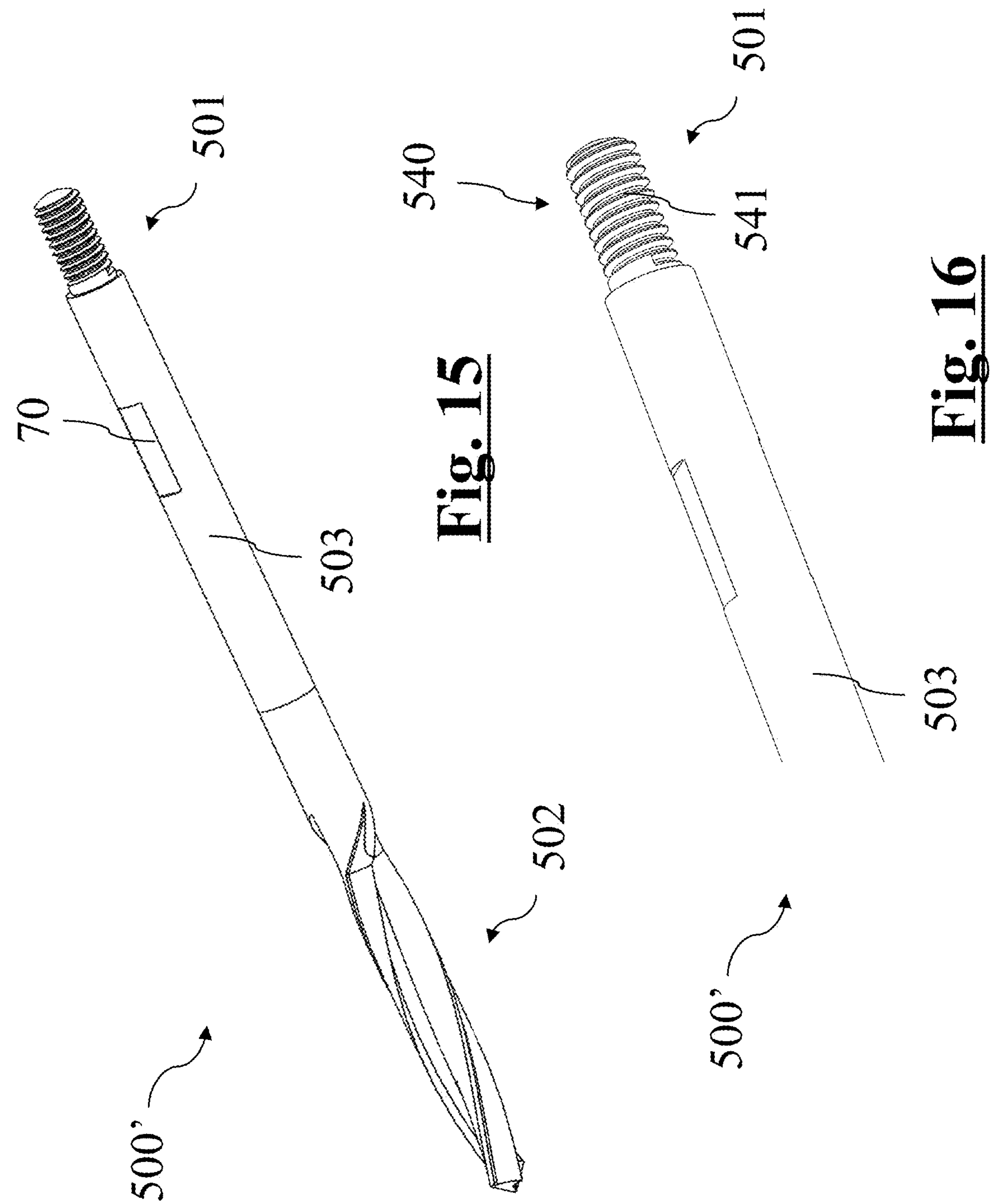
FIG. 15 shows a schematic perspective view of a second embodiment of a perforating tool provided in the accordance with the present invention.
FIG. 16 shows a schematic perspective view of the coupling end of the tool according to FIG. 15.

An alternative surgical technique may envisage the use of a perforating tool 500' which has a smaller length than that of the long bone in which it is inserted, such as that shown in FIGS. 15 and 16. The production of a shorter tool results in savings in terms of production costs.

Figure 17:
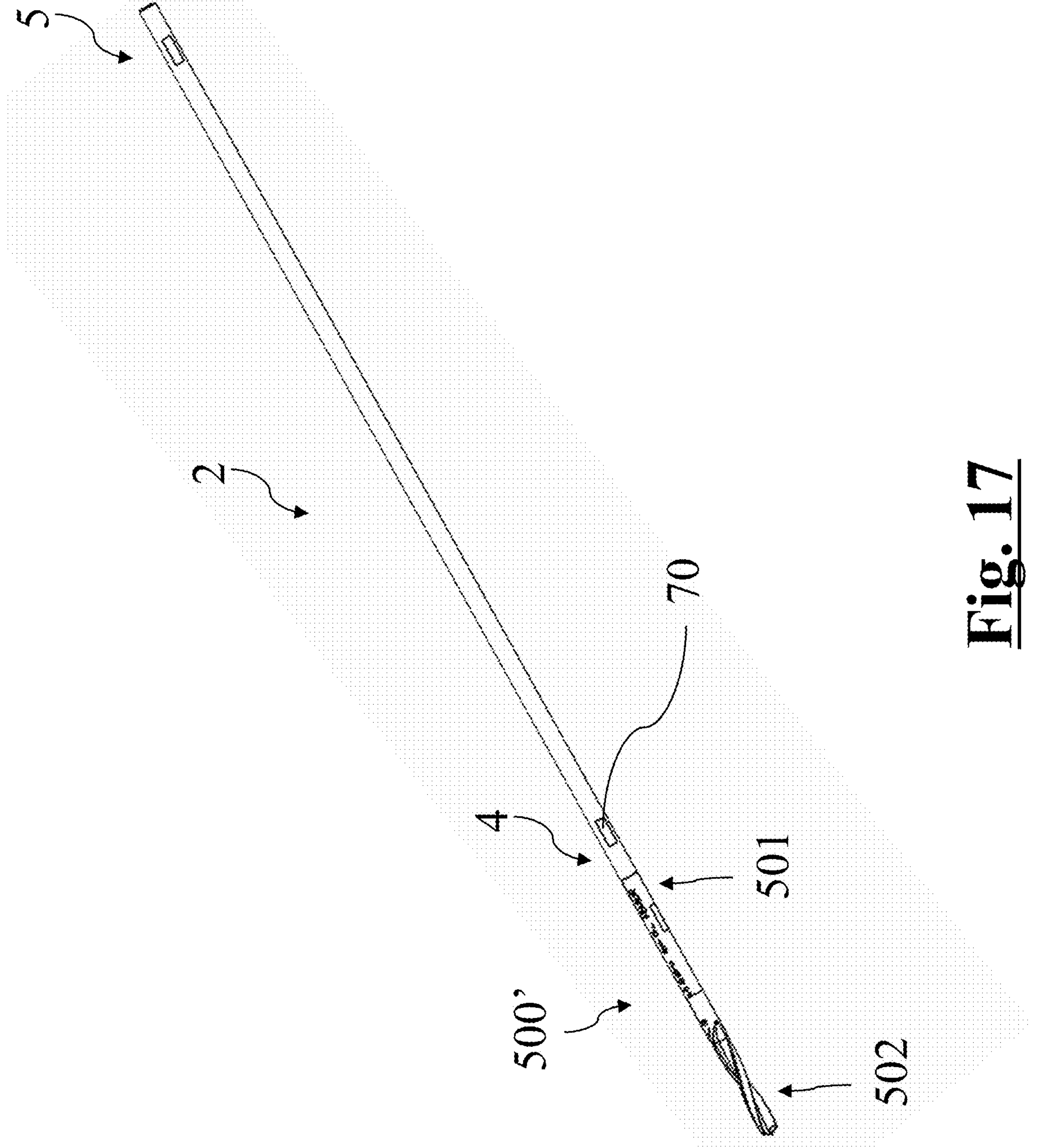
FIG. 17 shows a schematic perspective view of the assembly comprising the telescopic nail according to FIG. 1 and the tool according to FIG. 13, coupled together.

In this case the hollow stem 2 may be coupled to the coupling end 501 of the perforating tool 500 before the perforating tool 500 is inserted into the bone (see FIG. 17).

In particular, the perforating tool 500 may be supplied already assembled on the hollow stem 2, thus allowing the surgeon to dispense with this step and therefore reducing the number of operating steps.

In this case, during the advancing movement of the perforating tool 500', the hollow stem 2 of the telescopic nail 1 compensates for the smaller length of the tool, itself acting as an extension of the tool so as to guide the advancing movement.

From the above description it clearly emerges how the telescopic nail and the perforating tool according to the present invention achieve the predefined objects and result in numerous advantages compared to the devices of the prior art.

Obviously, the person skilled in the art may make numerous modifications and variations to the invention described above in order to meet any specific requirements which may arise, all of these being moreover contained within the scope of protection of the invention as defined by the following claims.

The invention claimed is:

1. A method for implanting a telescopic nail comprising:
providing a telescopic nail comprising:
- a hollow stem;
- a rod inserted telescopically into the hollow stem;
- a first fastening element configured to couple to an end of the hollow stem for fixing to a first long bone end;
- a second fastening element configured to couple to an end of the rod for fixing to a second long bone end;
- said end of the hollow stem being provided with a coupler for coupling to a coupling end of a perforating tool which is configured to be inserted into a cavity formed in the bone for insertion of the nail;

preparing said perforating tool, wherein the coupling end of the perforating tool comprises a counter-coupler designed to be coupled to said coupler of said end of the hollow stem of the telescopic nail;

inserting an end of the perforating tool opposite to the coupling end inside the cavity through an end of the bone;

coupling the coupler of said end of the hollow stem of the telescopic nail together with the counter-coupler of the coupling end of the perforating tool;

advancing the perforating tool inside the cavity until it comes out completely from the other long bone end, drawing along with it the hollow stem into the cavity; and uncoupling the perforating tool from the hollow stem.

2. The method according to claim 1, further comprising:

inserting an opposite end of the rod of the telescopic nail, opposite to the second fastening element, into the hollow stem through an opposite end of the hollow stem, said opposite end of the hollow stem being opposite to said end of the hollow stem.

3. The method according to claim 2, wherein said opposite end of the hollow stem comprises a coupler configured to couple to said counter-coupler of the coupling end of the perforating tool.

4. The method according to claim 1, further comprising:

coupling the first fastening element to said end of the hollow stem.

5. The method according to claim 4, further comprising:

fixing the first fastening element to the first bone end.

6. The method according to claim 5, further comprising:

fixing the second fastening element to the second bone end.

7. The method according to claim 1, wherein the perforating tool comprises a perforating end designed to form the cavity for insertion of the telescopic nail.

8. The method according to claim 7, wherein the coupling end of the perforating tool is opposite to the perforating end of the perforating tool.

9. Method according to claim 7, wherein the perforating end of the perforating tool is inserted into a distal end of the bone and the perforating tool is gradually advanced so as to form the cavity for inserting the telescopic nail, wherein the perforating tool is advanced until the perforating end emerges from a proximal end, opposite to said distal end, of the bone, leaving the coupling end of the perforating tool outside of the distal end of the bone.

10. The method according to claim 9, wherein the end of the hollow stem of the telescopic nail is coupled by screwing to the coupling end of the perforating tool and the perforating tool is extracted from the proximal end of the bone, being drawn along behind the hollow stem until the end of the hollow stem emerges from the proximal end of the bone.

11. The method according to claim 10, wherein, during this latter step, the rod is kept inserted inside the cavity of the hollow stem, ensuring structural continuity.

12. The method according to claim 10, wherein the perforating tool is then uncoupled from the hollow stem after the end of the hollow stem emerges from the proximal end of the bone.

13. The method according to claim 11, wherein the perforating tool is then uncoupled from the hollow stem after the end of the hollow stem emerges from the proximal end of the bone.

14. The method according to claim 1, wherein the cavity is formed during the insertion and advancing movement of the perforating tool inside the bone.

15. The method according to claim 1, wherein the step of coupling the coupler of the hollow stem with the counter-coupler of the perforating tool is performed before inserting the perforating tool into the bone.

16. The method according to claim 1, wherein the perforating tool has a smaller length than that of the long bone, to couple the hollow stem to the perforating tool and to insert the perforating tool using the same hollow stem as an advancing guide.

17. The method according to claim 1, wherein the coupler forms a threaded coupling with the coupling end of the perforating tool.

18. The method according to claim 1, the coupler comprises an internally threaded end of the hollow stem for receiving, by screwing, an external thread of the coupling end of the perforating tool.

19. The method according to claim 1, said first fastening element is structured as a screw with a shank to be coupled to said end of the hollow stem and a fixing head for fixing to the bone.

* * * * *